United States Patent
Wolde-Mariam

(10) Patent No.: US 6,720,160 B2
(45) Date of Patent: Apr. 13, 2004

(54) METHOD FOR SIMULTANEOUS DETECTION OF MULTIPLE MICROBIAL ANTIGENS IN BIOLOGICAL SPECIMENS FROM MASTITIC ANIMALS

(75) Inventor: Wondu Wolde-Mariam, Rowland Heights, CA (US)

(73) Assignee: Helica BioSystems, Inc., Fullerton, CA (US)

(*) Notice: Subject to any disclaimer, the term of this patent is extended or adjusted under 35 U.S.C. 154(b) by 4 days.

(21) Appl. No.: 09/976,512

(22) Filed: Oct. 11, 2001

(65) Prior Publication Data

US 2003/0073073 A1 Apr. 17, 2003

(51) Int. Cl.[7] .............................................. G01N 33/543
(52) U.S. Cl. .................... 435/7.32; 435/7.33; 435/7.34; 435/7.1; 435/7.92; 435/7.93; 435/7.94; 435/7.95; 435/287.1; 435/287.7; 435/970; 435/973; 436/514; 436/518; 436/810; 436/823; 424/237.1; 424/243.1; 424/244.1; 424/264.1
(58) Field of Search ................................. 436/514, 518, 436/810, 823; 435/7.1, 7.92, 7.93, 7.94, 7.95, 287.1, 287.7, 970, 973, 7.32, 7.33, 7.34; 424/237.1, 243.1, 244.1, 264.1

(56) References Cited

U.S. PATENT DOCUMENTS

| | | |
|---|---|---|
| 4,849,341 A | 7/1989 | Adams et al. |
| 5,026,638 A | 6/1991 | Saperstein |
| 5,132,210 A | 7/1992 | Adams et al. |
| 5,168,044 A | 12/1992 | Joyce et al. |
| 5,198,213 A | 3/1993 | Stott et al. |
| 5,198,339 A | 3/1993 | Hansen et al. |
| 5,225,331 A | 7/1993 | Jennings et al. |
| 5,550,030 A | 8/1996 | Tanaka et al. |
| 5,591,645 A | 1/1997 | Rosenstein |
| 5,798,273 A | 8/1998 | Shuler et al. |
| D404,812 S | 1/1999 | Cipkowski |
| 5,958,714 A | 9/1999 | Gordon et al. |
| 5,976,895 A | 11/1999 | Cipkowski |
| 5,976,896 A | 11/1999 | Kumar et al. |
| D420,141 S | 2/2000 | Casterlin |
| D423,110 S | 4/2000 | Cipkowski |
| D430,303 S | 8/2000 | Cipkowski |

FOREIGN PATENT DOCUMENTS

| | | |
|---|---|---|
| EP | 237 384 | 2/1987 |
| GB | 2314 625 A | 1/1998 |

OTHER PUBLICATIONS

Crist, et al. *Mastitis and its Control* University of Kentucky, College of Agriculture (Cooperative Extension Service), ASC–140, pp. 1–14, 1997.

Gilson, Warren *Interpreting and Using Mastitis Screening Tests* University of Georgia College of Agriculture & Environmental Sciences, Bulletin 913, pp 1–12, web site Aug. 21, 2002.

Gonzalez et al. *Polyclonal Antibodies Against Live Cells of Pseudomonas fluorescens for the Detection. . .* J. Dairy Sci. 77:3552–3557, 1994.

Gutierrez, et al. *Monoclonal Antibodies and an Indirect ELISA for Detection of Psychrotrophic Bacteria in Refrigerated Milk* Jr. of Food Protection, 60(1):23–27, 1997.

Jasper, et al. *Relationships Among the Results of Coagulase, Staphylococcal Toxin, and Thermonuclease Tests on Staphylococci from Cow Milk*, Jr. of Cl. Microbiology, Apr. 1985, 21(4):582–584.

Lipkin, et al. Abstract *Direct PCR Detection of Mastitis causing Pathogens in Milk* Research Dev. Co. of the Hebrew University of Jerusalem, A–0645.

Zorah, et al. *Detection of bacterial antigens in milk samples from clinical cases of bovine mastitis in which culture is negative* The Veterinary Record, pp. 208–210, Feb. 27, 1993.

Staphylococcus Latex Kit, Product codes: BA001, BA001.1, The Binding Site Limited, P.O. Box 4073, Birmingham, B29 6AT UK.

Inoculation & Interpretation it's a easy as 1–2–3, (kit) A.J. Buck & Son A Division of National Logistics Services LLC.

InTray Colorex Screen Test, BIOMED Diagnostics, 1430 Koll Circle, Ste. 101, San Jose, CA (Document No. 10–088).

Bramley, A.J. *Mastitis: Physiology or Pathology* Flem. Vet. J. 62, 1991 Suppl. 1, 3–113.

Byrne, et al., "Application of an indirect ELISA to milk samples to identify cows with Mycoplasma bovis mastitis", *The Veterinary Record*, Mar. 25, 2000, 146:368–369.

Chalifour, et al., "Use of defined oligosaccharide epitopes in an ELISA for group B streptococcus", *Jr. of Immunological Methods*, (1992) 154:69–76.

Donders, et al., "Accuracy of rapid antigen detection test for group B streptococci in the indigenous vaginal bacterial flora", *Arch Gynecol. Obstet.* (1999) 263:34–36.

Felten, et al., "Analyse Critique des Tests de Depistage rapide de Staphylococcus aureus, pastorex staph plus, slides staph–kit et staph aureus, dans les isolats cliniques", *Path. Biol.* (1995) 43:471–476.

(List continued on next page.)

Primary Examiner—Bao-Thuy L. Nguyen
(74) Attorney, Agent, or Firm—Knobbe, Martens, Olson & Bear, LLP

(57) ABSTRACT

The present invention involves a method and an immuno-analytical device for the rapid and simultaneous detection of multiple micro-organisms in the biological fluids from milk-producing animals suffering from mastitis. This method is based on a lateral flow immuno-assay technique performed to detect antigens specific for multiple infectious agents which are known to cause and/or be encountered in cases of mastitis. Mastitis is an inflammatory condition affecting the udders of milk-producing animals as a result of microbial infections.

23 Claims, No Drawings

OTHER PUBLICATIONS

Heller, et al., "Antigen capture ELISA using a monoclonal antibody for the detection of Mycoplasma bovis in milk", *Veterinary Microbiology*, (1993) 37:127–133.

Hordnes, et al., "Evaluation of a Rapid Enzyme Immunoassay for Detection of Genital Colonization of Group B Streptococci in Pregnant Women: Own Experience and Review", *Aust. NZ J. Obstet. Gynaecol.* (1995), 35(3):251–253.

Hotzel, et al., "Enhancement of Mycoplasma bovis detection in milk samples by antigen capture prior to PCR", *Molecular and Cellular Probes* (1999) 13:175–178.

Neyret, et al., "Evaluation of a Commercial Test Kit for Rapid Detection of Staphylococcus aureus in Blood Cultures", *Eur. J. Clin. Microbiol. Infect. Dis.*, (1997) 16:165–166.

Orden, et al., "Detection of enterotoxins and TSST–1 secreted by Staphylococcus aureus isolated from ruminant mastitis. Comparison of ELISA and Immunoblot", *Journal of Applied Bacteriology* (1992), 72:486–489.

Rosocha, et al., "Monoclonal Antibodies Against the Common Polysacchardie of Streptococcus agalactiae", *Folia Microbiol.* (1996) 41(5):436–440.

Sachse, et al., "Comparison of various diagnoistic methods for the detection of Mycoplasma bovis", *Rev. Sci. Tech. Off. Int. Epiz.* (1993) 12(2):571–580.

van Griethuysen, et al., "International Multicenter Evaluation of Latex Agglutination Tests for Identification of Staphylococcus aureus", *Jr. of Clinical Microbiology* (2001) 39(1):86–89.

Wichelhaus, et al., "Rapid Detection of Epidemic Strains of Methicillin–Resistant Staphylococcus aureus", *Jr. of Clinical Microbiology*, (1999) 37:690–693.

Yazdankhah, et al., "Development and evaluation of an immunomagentic separation–ELISA for the detection of Staphylococcus aureus thermostable nuclease in composite milk", *Veterinary Microbiology*, (1999) 67:113–125.

METHOD FOR SIMULTANEOUS DETECTION OF MULTIPLE MICROBIAL ANTIGENS IN BIOLOGICAL SPECIMENS FROM MASTITIC ANIMALS

RELATED APPLICATIONS

This application claims priority under 35 U.S.C. §119(e) of the U.S. Provisional Application that was originally filed as non-provisional U.S. application Ser. No. 09/811,806, filed Mar. 30, 2001.

FIELD OF THE INVENTION

The invention relates generally to the field of immuno-assays. More specifically, the invention relates to a simple, rapid inexpensive pathogen-specific immuno-assay method for simultaneously screening multiple infectious agents associated with mastitis, and inflammatory disease of the udder in milk-producing animals.

BACKGROUND OF THE INVENTION

Mastitis is a disease of cattle and other ruminants that, if not detected early, has adverse economic consequences to the dairy farmer. Estimated annual losses amount to $150–300 per cow per year with total annual losses in the U.S. ranging from $1.5 to $3.0 billion.

Untreated mastitis results in economic losses due to costs arising from reduced milk production, discarded milk, treatment and premature culling or death. This disease is found in four forms: acute, chronic, clinical, and sub-clinical. Sub-clinical mastitis, which shows no visible signs of disease, causes the greatest financial loss to dairy farmers. For every clinical case, there will be 15 to 40 sub-clinical cases, almost all of which progress to clinical cases. Chronic cases serve as a constant reservoir of pathogens causing mastitis.

Screening and evaluation of mastitis has been routinely performed utilizing the following procedures: California Mastitis Test (CMT, a cow-side test), Wisconsin Mastitis Test (WMT, a lab variant of the CMT), somatic cell count (SCC), strip test (cow-side test on foremilk), and milk cultures (a lab test). All but the last of these tests are non-specific indicators of inflammation and do not detect specific infectious agents. They are based on estimating or counting abnormal numbers of somatic cells, mostly white blood cells and epithelial cells found in milk suggestive of infections or injury. CMT test results can be elevated due to malfunctioning or misused milking equipment unrelated to bacterial infection. SCC requires expensive equipment and does not pinpoint infected quarters of the udder. Infectious agents, mostly bacteria, are only sought for and identified utilizing the milk culture procedure. It is laborious, expensive, and takes from 24 hours to 10 days to complete. It also requires samples collected aseptically which are difficult to obtain under field conditions where there are numerous sources of contamination.

In the patent literature, only one same-day test for bacterial identification in mastitis has been described. This is covered under U.S. Pat. Nos. 4,849,341 (Adams, et.al. Jul. 1989) and U.S. Pat. No. 5,132,210 (Adams, et.al. July 1992), and comprises a diagnostic test for detecting antibodies to *Staphylococcus aureus* utilizing a classic ELISA test format. Antibody detection is an indirect test and not necessarily specific for current infection. In addition, although it is one of the most important pathogens causing mastitis, *Staphylococcus aureus* is only one among many encountered. Similar test formats, mostly for antibody detection from single infectious agents found in mastitic milk, are also found in veterinary research publications with no mention of a simultaneous detection format for two or more organisms.

The following issues and problems summarize the current state of mastitis testing and unnecessary costs to the dairy farmer in lost time and resources.

1. Currently used CMT, WMT, SCC and strip tests do not identify pathogens. They are insensitive and non-specific cow-side testing methods. Mixed species of infectious agents, whose identification is essential to diagnosis of mastitis, are not identified on a timely basis using these presently popular techniques.

2. Culture tests for identifying pathogens take at least 24 hours and up to 10 days to obtain results. Such long turnaround on lab results does not allow timely identification of cows with poor (volume and quality) milk output and hence does not ameliorate economic losses.

3. Culture tests are laborious, expensive, and require aseptically collected milk to minimize occurrence of contaminants.

4. There is currently no pathogen-specific test for field (cow-side) use on the market. A simple and rapid test that can be used by untrained personnel and that can be stored under ambient conditions is badly needed.

5. There is no pathogen-specific field test to evaluate infections in all four quarters of the udder to pinpoint the source of poor quality milk or poor milk yield per cow.

6. There is no simple and rapid pathogen-specific test that can aid buyers and sellers of herds in identifying healthy and economically useful animals.

7. Currently available, non-pathogen specific methods do not provide any information on an appropriate therapeutic course that can be instituted in a timely manner.

Therefore, there is a need for a simple, low-cost test which will identify the presence of a variety of pathogens associated with mastitis.

SUMMARY OF THE INVENTION

A method for the simultaneous and rapid detection of multiple pathogens in the milk of animals with suspected mastitis is disclosed herein. The method uses pathogen-specific antibodies as detection tools. One embodiment of the method uses a lateral flow test format, allowing for at least 10 simultaneous tests on one card. Up to 10 lateral flow strips can be arranged on a typically-sized card. This embodiment allows the testing of animals in the field with almost immediate results.

One embodiment is a method for detecting a plurality of different pathogens in a milk sample of a mammal by exposing the milk sample to a plurality of different antibodies specific to an antigen from a pathogen of said mammal; and identifying whether the specific antibodies bind to one or more of the antigens, wherein the antigens are from a plurality of different pathogens. In a further embodiment, the milk sample is allowed to settle into two phases before exposing and wherein the top "clear" phase is exposed. Alternatively, the milk sample is diluted before exposing. The cream may be removed from the top of the milk before exposing. In one embodiment, the milk sample is treated to remove at least about 50% of the fat and/or the casein. The treatment may be by adding a detergent to remove the fat globules and/or by precipitating the casein with acid. The antibodies are specific for a pathogen which may be a bacteria, a virus, and a fungus. The milk-producing animal may be a cow, a sheep or a goat.

In one embodiment, the pathogen is a bacteria selected from the group consisting of: Streptococcus spp., Enterococcus spp., Staphylococcus spp., Micrococcus spp., *Escherischia coli,* Klebsiella spp. Enterobacteria, Serratia spp., Pseudomonas spp., Proteus spp., Pasteurella spp., *Corynebacterium bovis, Arcanobacterium pyogenes,* Mycobacterium spp., Bacillus spp., and Mycoplasma spp.

In a further embodiment, the pathogen is a yeast or a mold selected from the group consisting of: Nocardia spp. and Prototheca. The pathogen may be selected from the group consisting of: *S. agalactiae, S. dysgalactiae,* and *S. uberis* or *Staphylococcus aureus.* The pathogen may be a. coagulase-negative Staphylococcus. The mycoplasma may be selected from the group consisting of *M. bovis, M.californicum,* and *M.bovigenitaliae.*

In one embodiment, the antibodies are specific to antigens from at least 3 different pathogens. In a further embodiment the antibodies are specific to 7 pathogens. In a further embodiment the antibodies are specific to 7 pathogens. In one embodiment, the 3 pathogens are *Streptococcus agalactiae, Staphylococcus aureus,* and *Mycoplasma bovis.* In a further embodiment, the 7 pathogens are *Streptococcus agalactiae, Staphylococcus aureus, Mycoplasma bovis, Escherichia coli,* coagulase-negative Staphylococci, *M. californicum,* and *M. bovigenitaliae.*

In one embodiment, the method is a lateral flow test format.

A further embodiment is a kit for the detection of a plurality of pathogens in milk, having a plurality of antibodies, wherein said antibodies are specific to an antigen from a pathogen of milk, wherein said antigens are from a plurality of pathogens; and a marker for the binding of said antibodies to said antigen.

In one embodiment, the kit also has a container which allows the milk to be collected. The kit may also have cleaning products for the removal of organisms from the outside of a milk-producing organ. The kit may also have at least one antibody specific to antigens from granulocytes. The granulocytes may be neutrophils. The granulocytes may be a general indicator of mastitis.

DETAILED DESCRIPTION OF THE PREFERRED EMBODIMENT

A method for simultaneous and rapid detection of multiple pathogens in the milk of milk-producing animals with suspected mastitis is described. The method uses pathogen-specific antibodies as detection tools. One embodiment of the method uses a lateral flow test format. In direct contrast to those methods presently used, the method is fast, easy to use, and allows the detection of the pathogens in the field. In addition, the present methods of detection are expensive and require a highly skilled technician to perform and analyze the test, while the present method requires no training and could even be done by an employee or the owner of the dairy.

Further, this method offers the following advantages over the current state of mastitis testing:
1. Simultaneous and inexpensive identification of specific micro-organisms in one milk sample and in one simple operation, which is superior to current field tests that are not specific for mastitis-causing pathogens.
2. Rapid screening for specific pathogens in 1–15 minutes, which offers a major improvement over laborious lab tests that take from 24 hours to 10 days to obtain results.
3. Identification of specific pathogens, which leads to rapid decisions on whether to treat animals or to segregate them to minimize spread of infection. It can also provide information that may be helpful in choosing a course of treatment.
4. Early and rapid identification of organisms causing subclinical mastitis, which would result in early treatment and prevent progression to clinical mastitis.
5. Identification of specific organisms in animals with chronic mastitis, which will aid in making decisions to treat them or remove them from the herd in favor of eliminating the reservoirs serving as sources of infection.
6. Identification of specific organisms in animals with acute and clinical mastitis, which can lead to prompt treatment or culling.
7. A simple pathogen-specific field test that can be used by untrained personnel with no technical skills or knowledge of microbiology, which saves valuable time and resources.
8. Storage of test reagents and devices under ambient conditions, without requirement for refrigeration, which is ideal for field conditions.
9. A pathogen-specific test which allows for the separate evaluation of all quarters of the udder on a regular basis to confirm secretion of uninfected milk, which can lead to improved milk quality and yield per animal.
10. A pathogen-specific test that allows pre-testing before purchasing herds, which provides obvious advantages in economic outcome and also averts the co-mingling of infected animals in the herd.

Further objects and advantages will become apparent from the description below.

Pathogens

The pathogens which are to be identified herein may be any pathogen associated with mastitis in any milk-producing animal. The milk-producing animal may include such commercial milk-producers as cows, goats, and sheep.

However, the most common milk-producing commercial animal in industrialized nations is the cow. For that reason, the method will be explained using the cow as the exemplary animal. In addition, it is likely that many of the pathogens associated with bovine mastitis are also associated with mastitis of other commercial milk-producing animals.

The common pathogens associated with bovine mastitis include many types of bacteria, fungi, and viruses, however, they may also include protozoa and such pathogens as prions and viroids. A number of pathogens are known to cause mastitis at the present time. However, it is envisioned that the pathogens most commonly associated with mastitis may change in many ways. Emerging microbes may become new pathogens of the cow mammary gland, pathogens which previously were present but did not cause mastitis may develop the ability to cause disease, pathogens which were previously rarely associated with mastitis may become more common. These changes may occur for a number of reasons, including antibiotic use, genetic reassortment or mutation, incorporation of new toxins, antibiotic resistance, and the incorporation of the ability to infect a new species. However, the antigens associated with groups of pathogens may already be known or may be easily identified using techniques known to one of skill in the art as well as the teaching herein.

The most common pathogens associated with bovine mastitis include: Streptococcus spp. (including but not limited to *S. agalactiae, S. dysgalactiae, S. uberis*), Enterococcus, *Staphylococcus aureus* and coagulase-negative Staphylococci, Micrococcus, *Escherischia coli,*

Klebsiella spp. Enterobacteria, Serratia spp., Pseudomonas spp., Proteus spp., Pasteurella spp., yeasts and molds such as but not limited to Nocardia spp. and Prototheca, *Corynebacterium bovis, Arcanobacterium pyogenes,* Mycobacterium spp., Bacillus spp., and Mycoplasma spp. including but not limited to *M. bovis, M.californicum, M.bovigenitalium.*

Presently, the most common pathogens are those that are associated with clinical mastitis and include *Streptococcus agalactiae, Staphylococcus aureus,* and *Mycoplasma bovis.* However, those which are less common and those associated with sub-clinical mastitis, particularly because they are so numerous, make a very important contribution to the losses due to mastitis. Therefore, those that are most common at a given time or in a given area may be included within the test.

The most common of these includes *Streptococcus agalactiae, Staphylococcus aureus,* and *Mycoplasma bovis, Eschericia coli,* and coagulase negative Streptococcus spp.

However, the addition of a test for nonpathogenic Staphylococcus spp. is particularly useful since it is known that the presence of nonpathogenic Staphylococcus spp. predisposes the cow to the pathogenic strains such as *Staphylococcus aureus.*

In sheep and goats, presently, the most common organisms associated with mastitis includes: *Staphylococcus aureus,* non-hemolytic Staphylococci, *Mycoplasma capricola, M. mycoides* subspecies *mycoides,* and *M. putrefaciens.* Other possible agents of mastitis in sheep and goats include: *Mycoplasma agalactiae, M. arginini, M. conjunctivae, M. ovipnuemoniae,* and Mycoplasma strain F38.

Antigens

The choice of antigen for use in identifying the pathogens varies depending on the purpose. It is likely that a number of mastitic pathogens may share a common antigen. If the antigen is a component of those pathogens associated with mastitis with little or no cross-reactivity, then it can be used in the test. In particular, if it shows little or no cross-reactivity with normal flora, or other pathogens which may be associated with mastitis. However, it should exhibit no cross-reactivity with antigens naturally found in the milk.

For example, for *Staphylococcus aureus* antigens which may be detected include, but are not limited to: teichoic acid composed of N-acetyl glucosamine residues attached in either alpha or beta linkage to a polyribitol phosphate backbone, protein A, capsular polysaccharides, free coagulases, hemolysins (alpha, beta, gamma, delta), peptidoglycan, enterotoxins A, B, C, D, E, G, H, I, and TSST-1, exotoxins, fibronectin binding protein, thermostable nuclease, exfoliatin toxins (A&B), and leukocidin.

For *Streptococcus agalactiae* antigens which may be detected include, but are not limited to: hyaluronic acid capsule, cell wall proteins composed of M, T, R and other antigens, group-specific carbohydrate, N-acetyl glucosamine rhamnose, and mucopeptide (peptidoglycan).

For *Mycoplasma bovis* antigens which may be detected include, but are not limited to: membrane lipids containing glycolipids, neutral lipids, or polar lipids, membrane polysaccharides including lipopolysaccharides, membrane proteins including glycoproteins and membrane-bound enzymes, and cytoplasmic proteins.

Antibodies

Antibodies used herein include polyclonal, monoclonal and parts thereof. The parts, of necessity, are "active" parts or portions thereof. Active parts or portions thereof are those that can still recognize and bind to an antigen. However, the antibodies herein may recognize any antigen associated with mastitis pathogens including, but not limited to those disclosed herein under the heading "antigens":

Sample Collection and Handling

Collection of milk by aseptic techniques is an important first step in testing for mastitis-causing organisms. However, aseptic collection is confounded by the presence of microbial contaminants that can also cause disease. If contamination is suspected, re-sampling will be necessary.

It is envisioned that any method which results in a milk sample which is free of contamination can be used. However, the following steps are generally followed in the practice of sample milk collection:

First the teats from all quarters are thoroughly washed and dried. The foremilk is discarded, but observed for abnormalities suggestive of disease. The teats are predipped in disinfectant solution (predip solution) and contacted for at least 30 seconds. They are then dried thoroughly with paper towel followed by scrubbing teat-ends with alcohol-saturated cotton balls. Milk samples are collected into sterile tubes at a 45 degree angle and capped immediately. Generally 1–3 streams (about 2–3 mL) of milk is sufficient for testing. Samples from all quarters may also be combined by pooling into one tube. Finally, teats are dipped in a germicidal solution (teat dip) and samples are stored refrigerated or frozen for future testing.

Sample Treatment

The milk sample may be tested immediately, or alternatively, the sample may be allowed to sit for a while at room temperature or at 37° C. Often letting the sample sit for a while at room temperature is enough to allow the solids to settle, this leaves a "clearer" phase at the top, with the cream layer on top. The cream layer may be moved or skimmed off so as not to interfere with the test. In some cases, particularly when the cow is mastitic, the milk may have blood in it, or may have so much microbial activity that the consistency has changed. This may cause the milk to separate more easily into phases. For the preferred embodiment, a clear phase of about 1 cm is sufficient to allow for the lateral flow test. The cream layer may be removed or moved by any means known to one of skill in the art. In a field setting, it may be necessary to supply a sterile tool for removal of the cream, for example, a cardboard paper, filter paper, or a plastic tool. Alternatively, the milk sample may be treated with detergent and/or acid precipitated before sitting at room temperature, this may assist the process of separation.

Because milk contains fat globules and casein, it may be necessary to treat the milk sample prior to testing, particularly if the lateral flow embodiment is used. In some cases, simply diluting the milk in a buffer may allow for a correct reading. In one embodiment, the milk is treated to remove at least about 50% of the fat and/or casein. In a further embodiment, the milk is treated to remove between about 50% and about 100% of the fat and/or casein, including 55%, 60%, 65%, 70%, 75%, 80%, 85%, 90%, 95%, and 99%. This includes situations where for example 80% of the fat is removed and 50% of the casein is removed or variants thereof.

Dilution of the milk may include from about 1:1 to about 1:1000, including 1:2, 1:3, 1:4, 1:5, 1:6, 1:7, 1:8, 1:9, 1:10, 1:15, 1:20, 1:25, 1:30, 1:35, 1:40, 1:50, 1:60, 1:70, 1:80, 1:90, 1:100, 1:200, 1:300, 1:400, 1:500, 1:600, 1:700, 1:800, 1:900, and 1:950, and increments between.

If the fat and casein in the milk is interfering with the test, there are a variety of ways of treating the milk to allow testing. These methods include, but are not limited to the use of detergents or any other reagents which disrupt fat globules and any reagents which precipitate or remove casein. A low pH sample treatment buffer can be formulated in a matrix of standard buffers such as phosphate buffered saline or TRIS buffer and containing detergent (surfactants) or acids to facilitate the reduction or removal of interfering substances such as fat globules and casein respectively. Detergents may be used, such as Triton X-100 at concentrations from about 0.1 to about 2%, Triton-X-114 at concentrations from about 0.1 to about 2%, sodium dodecyl sulfate at concentrations from about 0.1 to about 2.0%, or sodium lauryl sarcosinate at concentrations from about 0.1 to about 2%, all of the detergents including 0.2, 0.3, 0.4, 0.5, 0.6, 0.7, 0.8, 0.9, 1.0, 1.1, 1.2, 1.3, 1.4, 1.5, 1.6, 1.7, 1.8 and 1.9% Bile salts may also be used in addition to or in place of detergent. Bile salts which may be used include, but are not restricted to: sodium deoxycholate from about 0.4 to about 3 mM, deoxycholic acid from about 0.5 to about 3 mM and/or taurodeoxycholate from about 0.5 to about 3 mM, all of the bile salts including 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, and 2.9 mM. Bile salts act by disrupting fat globules or by removing the outer membrane of eukaryotic cells. Casein may be precipitated by acidifying milk with incorporated lactic acid to bring the pH below 4.3. HCl, sulfuric acid or vinegar can also be used.

A column might be used, however, it may trap the bacteria and interfere with the test. Alternatively, beads which are specifically trap casein and fat globules may be added to the milk sample to remove these substances.

A pre-treatment buffer such as an isotonic phosphate buffered saline may be used. The buffer may contain reagents for disrupting milk fat globules and reducing the amount of casein that may interfere in the antibody-antigen reaction occurring on the lateral flow device.

The milk fat globules can be disrupted using any reagents known to one of skill in the art which disrupt fat globules without interfering with the test. Such reagents include, but are not limited to, one or a combination of non-ionic detergents at optimal concentrations. These detergents may include: Triton-X 100, Triton-X 114, sodium deoxycholate, sodium deoxycholic acid, sodium dodecyl sulfate, or sodium lauryl sarcosinate.

Casein may be diluted, removed or precipitated. Precipitation of casein can be performed using any one or a combination of weak acid reagents that can be selected from but not limited to: hydrochloric acid, sulfuric acid, acetic acid including vinegar, or lactic acid used at optimal concentration which does not interfere with the antigen-antibody complex.

The amount of each reagent and buffer depends on the milk sample used. However, in one embodiment, the milk sample is mixed at a one to one ratio with the pre-treatment buffer and allowed to settle for a time long enough to form two distinctly visible phases. This may take at least 5–15 minutes prior to testing. Separation of the sample to at least two distinctly visible phases including a relatively clear or translucent phase is a clear signal of the readiness for testing with the lateral flow device. However, a relatively clear sample may not be necessary for testing.

Methods

A number of methods for identifying pathogens or antigens using antibodies are known including western blots, RIA, ELISA, and FACS. However, any method may be used which identifies a pathogen based on the binding of a specific antibody to a pathogen-specific antigen.

One embodiment is a lateral flow immunochromatographic assay ("lateral flow immunoassay") such as that depicted in U.S. Pat. Nos. 5,976,895 (Cipkowski, November 1999), Des. 404,812 (Cipkowski, January 1999), Des. 423,110 (Cipkowski, April 2000), and Des. 430,303 (Cipkowski, August 2000) (all herein incorporated by reference). The format described in these patents was originally developed for the rapid and simultaneous detection of illicit drugs, but can be modified to identify pathogens in biological fluids. Other current applications of this assay format include testing in the area of food safety, plant and crop diseases, environmental contamination and biological warfare. In clinical assays in humans or animals, the sample used may be blood, urine, serum, milk, saliva, or CSF or external samples such as treated swabs. Assays may potentially be quantitative, semi-quantitative or qualitative. Generally, semi-quantitative and qualitative tests do not require any reading technology to be employed, and as such are ideal for use in the field, in clinics or in the home. Often these assays can be made simple enough to allow their use by untrained or minimally trained personnel in these settings.

The lateral flow immunoassay format can be rapid, inexpensive and can allow concurrent detection of multiple analytes. In the case herein the analytes are antigens from bacteria and other infectious agents that may be found in mastitis cases.

Examples and methods of making lateral flow formats can be found in U.S. Patent Applications: Shuler, et al., U.S. Pat. No. 5,798,273 and Rosenstein et al, U.S. Pat. No. 5,591,645 (both of which are herein incorporated by reference).

Briefly, for this specific application, the test device that incorporates the lateral flow technique is designed to contain specific antibody molecules that could be either monoclonal or polyclonal in origin. Each test contains a pair of antibodies, one of which is immobilized in a test line on a membrane (the capture antibody), and the second which is conjugated to a signal reagent designed to allow for the visualization of the assay endpoint, such as colloidal gold or colored latex micro-spheres. Enzyme or fluorescent labels may also be used to visualize the end-point of the reaction. The conjugate is removably attached to a separate pad which is overlapped onto the membrane impregnated with the capture antibody. When the assay is run by the addition of a sample and/or a buffer solution, the conjugate is re-mobilized and can flow by capillary action onto the membrane. The conjugate binds with the antigen of interest in the sample, and the antigen and conjugate are subsequently captured and precipitated by the immobilized antibody on the membrane. The end of the reaction is visualized by coloration on the membrane (specific drawing are found in the above-identified patent applications). If there is no antigen, the conjugate does not bind and is eluted further upstream into a wick.

Typically, each test is for a single pathogen, however, within that test, one or more antigens may be detected. For example, the antibodies which are used to detect the organism may contain more than one monoclonal antibody or may contain polyclonal antibodies. In this way a stronger reaction may be produced.

An alternative format for the test is as follows: each of the test strips is a one-step immunoassay in which a specially labeled antigen or antigen conjugate, competes with antigens which may be present in the sample for the limited number of binding sites on an antibody. The test strip consists of a membrane strip onto which an antigen conjugate has been immobilized. A colloidal gold-antibody complex is dried at one end of the membrane. In the absence of the antigen in the milk sample, the colloidal gold-antibody complex moves with the milk sample by capillary action to contact the immobilized antigen conjugate. An antibody-antigen reaction occurs forming a visible line in the test area. The formation of a visible line in the test area occurs when the test is negative for the antigen. When the antigen is present in the milk sample, the antigen will compete with the immobilized antigen-conjugate in the test area for the limited antibody sites on the colloidal gold-labeled antibody complex. If a sufficient amount of antigen is present, it will fill all of the available binding sites, thus preventing attachment of the labeled antibody to the antigen conjugate. An absence of a color line or band in the test area is indicative of a positive result. A control band or line comprised of a different antibody/antigen reaction is present on the membrane strip. The control line is not influenced by the presence or absence of the antigen in the milk and therefore should be present in all reactions. Thus, in some cases, the lateral flow technique can be used to partially quantitate the amount of antigen in the sample.

The advantages of the lateral flow assay format and accompanying sample collection device envisaged for this particular application include the following:

1. Simultaneous side by side testing for multiple analytes either on a single strip or on multiple side-by-side strips;
2. Rapid testing, with results potentially available within 30 minutes;
3. The ability to collect and test a sample in a single, sterile, enclosed device, thereby removing the requirement for sample transfer to additional containers for testing. This reduces the complexity of the assay and the potential for contamination of the sample, while also minimizing the difficulties of disposal of potentially biohazardous samples following testing;
4. The test is easy to perform and can be performed in the field by minimally trained personnel;
5. Results are easily read and interpreted by eye. No instrumentation is required for a qualitative or semi-quantitative test;
6. The format allows the flexibility to add more tests, up to ten per lateral flow unit are embodied in the referenced format;
7. Lateral flow assays commonly do not require refrigeration or other controlled storage conditions while in their original packaging. This further enhances their appeal for use in the field.

The abundance of antigen targets present in all mastitis-causing pathogens allows innumerable embodiments or antibody combinations and permutations, arrangements and configurations on lateral flow strips, and a permutation of unique pairings of capture antibodies and conjugated tracer antibodies.

Other types of specific tests can also be envisioned. For example, a format which tests only for clinical mastitis, or environmental mastitis. An environmental mastitis test would mainly be used to analyze the unsanitary conditions that cows inhabit. Causative bacterial agents are subclassified into coliforms and environmental streptococci. The most common coliforms include but are not limited to: *E. coli, Klebsiella pneumoniae, K. oxytoca,* and *Enterobacter aerogenes.* The most common Streptococci include but are not limited to: *Streptococcus uberis, S. bovis, S. dysgalactiae, Enterococcus faecalis* and *Enterococcus faecium.*

Test for Specific Pathogens and Non-specific Inflammation

Alternatively, a test may be incorporated which identifies the presence of somatic cells in the milk in addition to the specific antigens. Thus, while the dairyman is testing for specific pathogens, they may also get an idea of the somatic cell count, a familiar test for the dairyman. With this added test, the method allows analysis of nonspecific inflammation at the same time it is testing for specific pathogens. The antibodies are those specific for one or more type of somatic cells, ie: antibodies to cow, sheep, goat, or other mammal's granulocytes.

The present device can thus also comprise a non-pathogen specific component in addition to the pathogen specific tests. The chosen non-specific test is the somatic cell test.

Somatic cell detection and enumeration is widely used as a screening method for clinical and subclinical mastitis. Current variants of this parameter include the qualitative California Mastitis Test (CMT) and the Wisconsin Mastitis Test (WMT), as well as the quantitative Somatic Cell Test (SCC). The somatic cells detected by these methods consist of granulocytes, lymphocytes and epithelial cells that accumulate in the udder in response to bacterial infections causing mastitis. Of these cells, the number and proportion of granulocytes is the most abnormally elevated and hence a good target for a single analyte to measure in lieu of a total somatic cell count. Determination of the granulocyte load in milk from mastitic animals can therefore be incorporated as an additional screening parameter complementing the pathogen-specific tests in the lateral flow device. The advantage lies in the familiarity of the somatic cell count as the most widely accepted screening test to the users of this test and can provide them with a comparison as well as a control parameter.

This test can be incorporated in the lateral flow device in the same manner used for capturing microbial cells and tracking them with conjugated antibodies. Briefly, in the case of a test for cow's milk, an anti-bovine granulocyte antibody is bound to the nitrocellulose membrane on the lateral flow device and functions as a capture antibody reacting with granulocytes in the milk sample being tested and creating a "bound complex". A second anti-bovine granulocyte antibody that has been conjugated to colloidal gold or latex particles reacts with the bound complex and gives a signal as described for the detection of bound bacteria described in this document. The assay parameter allows detection of granulocyte numbers that are in the significant range defining clinical and subclinical mastitis. Although this parameter will be defined more accurately through clinical trials, the rule of thumb cell count in SCC tests is on the order of 300,000–400,000 cells per milliliter. The lateral flow assay for granulocytes will therefore be calibrated to this value in order to correspond to familiar variants of the somatic cell count.

The anti-granulocyte antibodies are any type of antibody which recognizes an antigen typically found on granulocytes. However, in one embodiment, an anti-granulocyte antibody is polyclonal in origin and raised by immunizing host animals (e.g. rabbits, goats, sheep) with purified bovine granulocytes from the blood of cows. There are a number of granulocyte purification protocols in the scientific literature that can be applied in order to produce material for raising antibodies.

A further embodiment which allows for enhancement of this testing protocol is by adding a test for the measurement of bovine lymphocytes and epithelial cells using appropriate antibodies that may be polyclonal or monoclonal in origin.

As a test offered side by side with the pathogen-specific tests, this addition will give the user a familiar measured index corresponding to the presence of mastitis in the udder as well as knowledge of specific pathogens causing the mastitic condition.

The following examples depict four embodiments which can be used in constructing a test. Specific examples of possible embodiments are provided below using *Staphylococcus aureus* as a representative organism. Similar scenarios can be provided for other pathogens and embodiments.

Antibodies:
1. Antibodies used in the lateral flow format may be prepared as a cocktail of two or more antibodies with specificity to any or a combination of antigen targets listed above for each pathogen. For example, a specific embodiment for *Staphylococcus aureus* may contain a plurality of antibodies recognizing exotoxin C plus alpha-hemolysin plus beta-hemolysin plus TSST-1 in one solution and impregnated in the lateral flow membranes as capture antibodies or as tracer antibodies conjugated to colloidal gold or similarly acceptable conjugates.
2. Antibodies used in the lateral flow format may be presented as a series of antibodies to specific antigen targets arranged on lateral flow strips side by side. For example, a specific embodiment may contain an antibody on each strip specific to any one antigen target such as exotoxin C, alpha-hemolysin, beta-hemolysin, or TSST-1 and impregnated in the lateral flow membranes as capture antibodies or as tracer antibodies conjugated to colloidal gold or similarly acceptable conjugates.
3. An additional embodiment may contain a combination of the above two embodiments. For example, a specific embodiment may contain a plurality of antibodies recognizing exotoxin C plus alpha hemolysin plus beta hemolysin on one strip and TSST-1 on a second strip and impregnated in the lateral flow membranes as capture antibodies or as tracer antibodies conjugated to colloidal gold or similarly acceptable conjugates.
4. An alternative embodiment of No. 3 above may contain a plurality of antibodies or a single antibody as a capture antibody and a second set of plural antibodies or one antibody as conjugated antibody. For example, a specific embodiment may contain a plurality of antibodies recognizing exotoxin C plus alpha hemolysin plus beta hemolysin as a capture antibody cocktail and anti-TSST-1 as a tracer antibody conjugated to colloidal gold and placed on the same lateral flow strip.

Many more combinations, permutations, arrangements and configurations on lateral flow strips, and permutations of unique pairings of capture antibodies and conjugated tracer antibodies are possible in devising alternative embodiments and are not limited to the examples above. In addition, there are many possibilities with regards to antibodies and fragments thereof, conjugating reagents and techniques thereof, placement, position on the membrane strips, and other variables. Thus, it is to be understood that various additions, deletions, modifications, and alterations may be made to the preferred embodiment in devising alternative embodiments.

The antibodies used are ones with specificity to each of two or more of the following micro-organisms encountered in mastitis conditions: Streptococcus spp. (including but not limited to *S. agalactiae, S. dysgalactiae,* and *S.uberis*), Enterococcus, *Staphylococcus aureus* and coagulase-negative Staphylococci, Micrococcus, *Escherischia coli,* Klebsiella spp. Enterobacteria, Serratia spp., Pseudomonas spp., Proteus spp., Pasteurella spp., yeasts and molds such as but not limited to Nocardia spp. and Prototheca, *Corynebacterium bovis, Arcanobacterium pyogenes,* Mycobacterium spp., Bacillus spp., and Mycoplasma spp. including but not limited to *M. bovis, M.californicum, M.bovigenitalium.* In one embodiment, the antibodies are specific to *Streptococcus agalactiae, Staphylococcus aureus,* and *Mycoplasma bovis.* In a further embodiment, the antibodies are specific to *Streptococcus agalactiae, Staphylococcus aureus, Mycoplasma bovis* and Staphylococcus spp (including non-coagulase positive Staphylococci.

The embodiment of the lateral flow immuno-assay described in U.S. Pat. No. 5,976,895 and corresponding design patents Des. 404,812, Des. 423,110, and Des. 430, 303 is particularly useful because it comprises: 1) a sample collection cup compatible in shape and orientation with, 2) a set of testing strips arranged longitudinally and side by side. Both of these components enable clean and easy assay performance in the field to give the desired outcomes. The sample collection cup allows presentation of sample milk or other biological fluids in a volume sufficient to immerse all strips contained on the test device. The parallel arrangement of test strips enables simultaneous testing for multiple pathogens.

Therefore, in a further embodiment, a kit is provided which includes a multiple test strip with or without a cup. The kit may also include directions for use or alternatively, the directions may be included on the cup or the back of the multiple test strip. The kit may also include a positive control, for example for a milk protein, to determine whether the milk or biological sample is usable. The kit may also contain a cleaning method, such as a packaged alcohol wipe to prepare the udder for obtaining the sample. The kit may also include a reusable bag for containing and disposing of any contaminated sample or kit paraphernalia.

EXAMPLE 1

The Making and Use of a Lateral Flow Immuno-assay for *Streptococcus agalactiae, Staphylococcus aureus,* and *Mycoplasma bovis*

The test strips contain antibodies specific for the following three infectious agents: *Streptococcus agalactiae, Staphylococcus aureus,* and *Mycoplasma bovis.*

The following steps take place on the surface of the device in order to complete the testing procedure:
1. A biological sample including, but not limited to, milk is placed in the sample collection cup.
2. The sample is then brought in contact with the lateral flow device by immersion of the parallel-arranged strips in the device into the milk sample.
3. The sample and strips are left in contact for at least 1 minute or up to 15 minutes.
4. The strips are then withdrawn from the cup.
5. A positive reaction is revealed when coloration develops in the specific location(s) representing each microorganism detected.

EXAMPLE 2

A Mastitis Kit

The kit contains the following: 1) a sample collection cup compatible in shape and orientation with, 2) a set of testing strips arranged longitudinally and side by side. Both of these components enable clean and easy assay performance in the field to give the desired outcomes. The sample collection cup allows presentation of sample milk or other biological fluid in a volume sufficient to immerse all strips contained on the test device. The parallel arrangement of test strips enables simultaneous testing for multiple pathogens.

EXAMPLE 3

Method for Preparation of Antibodies used as Probes in the Lateral Flow Assay

For *Staphylococcus aureus* and *Mycoplasma bovis*: Antibody reagents for each organism were raised and prepared by conventional methods. Briefly, organisms were grown in culture media in large quantities, harvested in late log phase and washed several times in an isotonic solution such as phosphate buffered saline (PBS), pH 7.2–7.4. The organisms were then killed by addition of 1.5% formalin and stirred for 90 minutes, centrifugally concentrated and, resuspended in PBS followed by heat treatment at 80° C. for 5 minutes. The organisms were readjusted to 100 million cells per mL and used to immunize rabbits. The immunogen was prepared with Freund's complete adjuvant. The rabbits were bled after 14 days and tested for antibody response and boosted on the $21^{st}$ day with more immunogen prepared with Freund's incomplete adjuvant, test bled at day 30, boosted again at 42 days, tested at day 50 with a final bleed at day 70.

Blood from days 50 and 70 were pooled and serum was separated by centrifugation. Serum IgG was obtained by protein A purification and further purified by affinity column prepared from the immunizing material. The eluted material contained antibodies with high specificity to either *Staphylococcus aureus* or *Mycoplasma bovis*.

These antibodies were used as capture antibodies at optimal concentrations after determination by checkerboard titrations. For use as tracer antibodies, they are conjugated to colloidal gold or colored latex spheres at optimal concentrations using the conventional chemistries for conjugate development.

Alternatively, monoclonal antibodies with specificities to various epitopes can be purchased from QED Bioscience (San Diego, Calif.). Procedures used for producing hybridomas and harvesting monoclonal antibodies are available from the manufacturer.

For *Streptococcus agalactiae*: Antibody reagents were purchased from Virostat (Portland, Me.). The manufacturer used conventional procedures similar to the steps described above to generate the highly specific antibodies.

The disclosed method, which is concerned with a same-day pathogen-specific screening test for mastitis, is a major departure from the non-specific methods now widely used. Accordingly, this method enables the rapid, inexpensive, and simultaneous detection of multiple bacteria and other infectious agents that may be found in most or all mastitis cases using a lateral flow immunoassay technique. The scope of this method ranges from a simple tool for inexpensive diagnostic screening to an effective measure that will bring significant economic benefits to the dairy industry in general and the dairy farmer in particular.

One embodiment is based on an established technology known as lateral flow immunoassay or immunochromatography that has been shown to be simple, fast and user friendly in many commercially successful diagnostic products. The method may also provide a new awareness of specific causes of mastitis in milk-producing animals and can be modified to be of specific use to a specific country, region, or even a specific milk-producing animal.

Thus the scope of this invention should be determined by the appended claims and knowledge of one of skill in the art. Accordingly, it is to be understood that various additions, deletions, modifications, and alterations may be made to the above-referenced embodiment without departing from the intended spirit and scope of the invention. It is, indeed, intended, that all such modifications alterations and deletions be included within the scope of the claims.

What is claimed is:

1. A method for simultaneously detecting a plurality of different indicators of mastitis in a milk sample of a mammal, comprising the steps of:
   exposing said milk sample to a test membrane having antibodies that specifically bind to a plurality of different pathogens selected from the group consisting of a Streptococcus species, a Staphylococcus species, and a Mycoplasma species; said test membrane further having antibodies that specifically bind to granulocytes in said milk sample;
   detecting the presence or absence of the pathogens and the amount of granulocytes in said milk sample; and
   relating the presence of said pathogens and said granulocytes in said milk sample to mastitis in said mammal.

2. The method of claim 1 wherein the milk sample is allowed to settle into two phases before exposing and wherein the top "clear" phase is exposed.

3. The method of claim 1 wherein the milk sample is diluted before exposing.

4. The method of claim 1 wherein the cream is removed from the top of the milk before exposing.

5. The method of claim 1 wherein said milk sample is treated to remove at least about 50% of the fat and/or the casein.

6. The method of claim 5 wherein said treatment comprises adding a detergent to remove the fat globules and precipitating the casein with acid.

7. The method of claim 1 wherein said milk-producing animal is a cow, a sheep or a goat.

8. The method of claim 1 wherein said Streptococcus species is selected from the group consisting of *S. agalactiae, S. dysgalactiae* and *S. uberis*.

9. The method claim 1 wherein said Staphylococcus species is a *Staphylococcus aureus*.

10. The method of claim 1 wherein said Staphylococcus species is a coagulase-negative Staphylococcus.

11. The method of claim 1 wherein said Mycoplasma is selected from the group consisting of *M. bovis, M. californicum,* and *M. bovigenitaliae*.

12. The method of claim 1 further comprising antibodies specific to at least 7 pathogens.

13. The method of claim 1 further comprising antibodies specific to at least 10 pathogens.

14. The method of claim 12 wherein said 7 pathogens are *Streptococcus agalactiae, Staphylococcus aureus, Mycoplasma bovis, Escherichia coli,* coagulase-negative Staphylococci, *M. californicum,* and *M. bovigenitaliae*.

15. The method of claim 1 further comprising a lateral flow test format.

16. The method of claim 15, further comprising:
   identifying the presence of the pathogens using second antibodies which are free to move by capillary action within the membrane.

17. The method of claim 16, wherein said second antibodies are conjugated to a marker.

18. The method of claim 17, wherein said marker is a color-producing agent.

19. The method of claim 18, wherein said color-producing agent is colloidal gold or a colored latex micro-sphere.

20. The method of claim 16, wherein said more than one test membrane is arranged longitudinally side by side.

21. The method of claim 16, wherein said method allows concurrent visualization of test results.

22. The method of claim 1, wherein said antibodies are polyclonal, monoclonal, or antigen-binding fragments thereof.

23. The method of claim 1, wherein said granulocytes are neutrophils.

* * * * *